United States Patent
Cutler

(10) Patent No.: US 10,213,270 B2
(45) Date of Patent: Feb. 26, 2019

(54) SMALL DISPOSABLE TORQUE LIMITING DRIVING TOOL WITH RUBBER GRIP

(71) Applicant: Brian James Cutler, Rowland Heights, CA (US)

(72) Inventor: Brian James Cutler, Rowland Heights, CA (US)

(73) Assignee: Lomack Industrial Co. Ltd., Hong Kong (HK)

( * ) Notice: Subject to any disclaimer, the term of this patent is extended or adjusted under 35 U.S.C. 154(b) by 250 days.

(21) Appl. No.: 15/367,175

(22) Filed: Dec. 2, 2016

(65) Prior Publication Data

US 2017/0156813 A1 Jun. 8, 2017

Related U.S. Application Data

(60) Provisional application No. 62/262,223, filed on Dec. 2, 2015.

(51) Int. Cl.
*A61B 90/00* (2016.01)
*B25B 23/14* (2006.01)
*B25B 23/142* (2006.01)
*A61B 17/88* (2006.01)

(52) U.S. Cl.
CPC .......... *A61B 90/03* (2016.02); *A61B 17/8875* (2013.01); *A61B 90/06* (2016.02); *B25B 23/141* (2013.01); *B25B 23/1427* (2013.01); *A61B 2090/031* (2016.02); *A61B 2090/066* (2016.02)

(58) Field of Classification Search
CPC . B25B 23/141; B25B 23/142; B25B 23/1422; A61B 90/03; A61B 90/06; A61B 2090/031; A61B 2090/066
See application file for complete search history.

(56) References Cited

U.S. PATENT DOCUMENTS

| | | | | |
|---|---|---|---|---|
| 4,262,501 | A * | 4/1981 | Vaughn | F16D 7/08 464/36 |
| 7,334,509 | B1 * | 2/2008 | Gao | B25B 15/02 81/467 |
| 9,132,536 | B2 * | 9/2015 | Nino | A61B 17/8883 |
| 9,241,751 | B2 * | 1/2016 | Nino | B25B 13/466 |
| 9,242,357 | B2 * | 1/2016 | Nino | B25B 23/141 |
| 9,259,258 | B2 * | 2/2016 | Laurenti | B25B 23/1427 |
| 9,409,285 | B2 * | 8/2016 | Ivinson | A61B 17/8875 |
| 9,445,873 | B2 * | 9/2016 | Nino | A61B 17/8883 |
| 9,446,507 | B2 * | 9/2016 | Nino | A61B 17/8875 |
| 9,931,741 | B2 * | 4/2018 | Nino | A61B 17/320016 |
| 2006/0162510 | A1 * | 7/2006 | Lee | B25B 23/141 81/475 |

(Continued)

*Primary Examiner* — David B Thomas
(74) *Attorney, Agent, or Firm* — James A. Italia; Italia IP

(57) ABSTRACT

A torque applying tool suited for torquing small surgical fasteners. The tool includes a torque limiting clutch accessible when a housing of the tool is removed, so that torque limits can be sensed without subjecting the blade or working shaft to deforming forces. Torque can be adjusted by turning a nut threaded to the blade or working shaft. The torque limiting clutch is formed in interacting cam members bearing interacting ratchet surfaces, the cam members urged together by a spring located between the clutch and the housing, away from interference with torque sensing when first establishing a predetermined maximum torque of the tool. The tool is small and disposable, and includes a rubber grip coating.

15 Claims, 2 Drawing Sheets

(56) References Cited

U.S. PATENT DOCUMENTS

| | | | |
|---|---|---|---|
| 2013/0276597 A1* | 10/2013 | Ivinson | B25B 13/46 |
| | | | 81/467 |
| 2016/0236335 A1* | 8/2016 | Hsieh | B25B 23/141 |
| 2016/0354581 A1* | 12/2016 | Ivinson | A61M 25/0113 |
| 2017/0056075 A1* | 3/2017 | Annadanam | A61B 90/06 |
| 2017/0105813 A1* | 4/2017 | Rash | A61B 17/8875 |

* cited by examiner

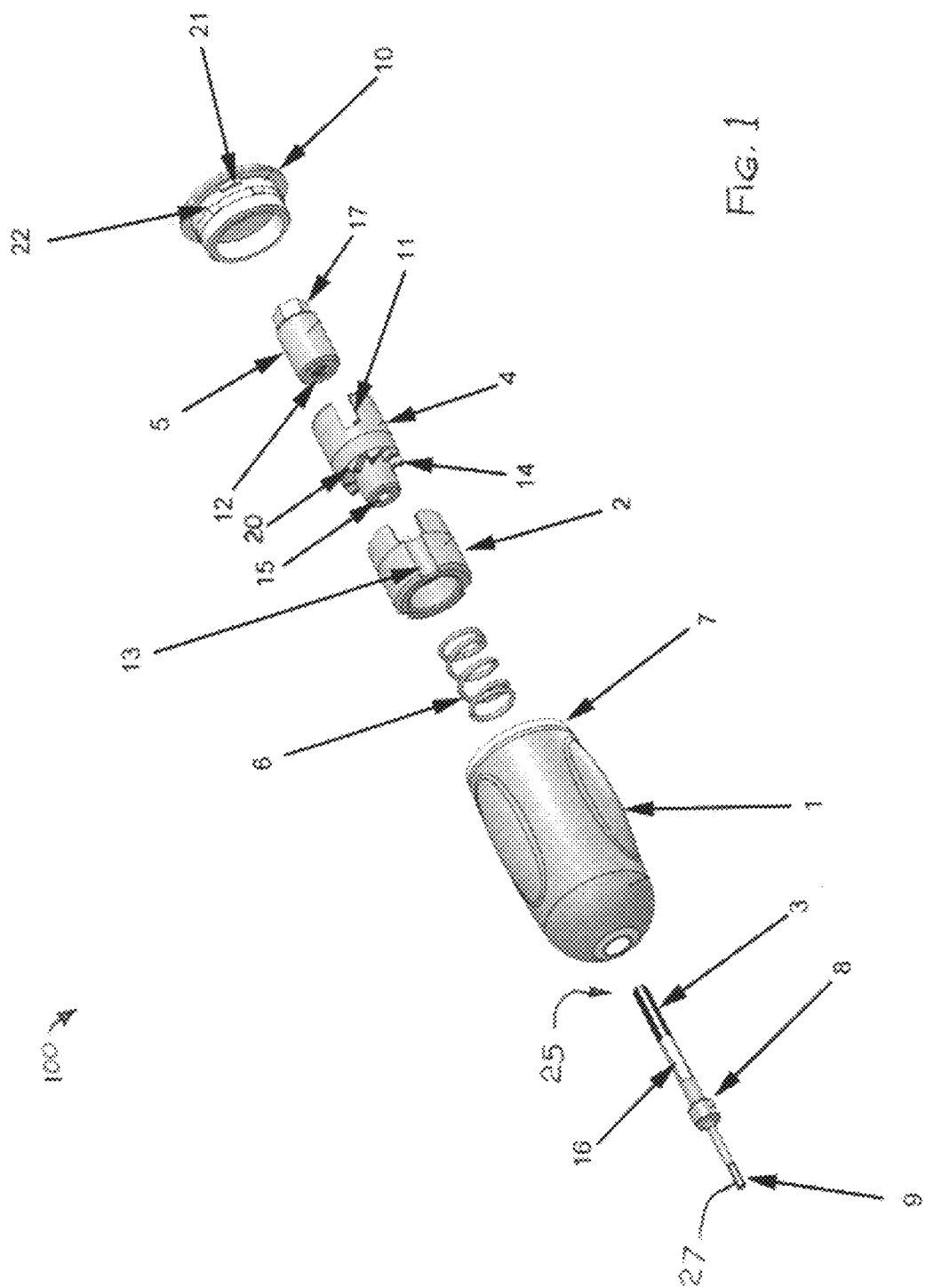

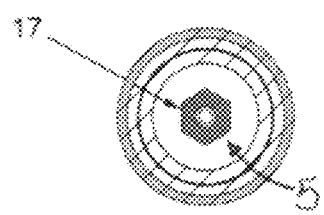
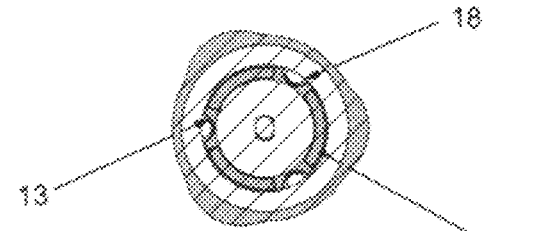
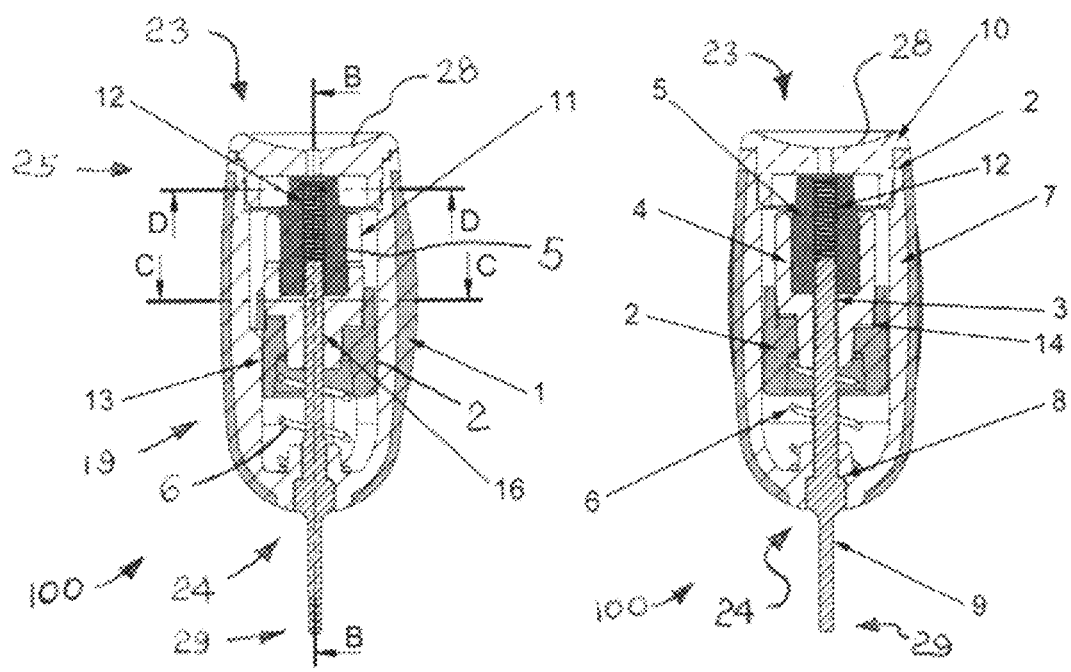

SMALL DISPOSABLE TORQUE LIMITING DRIVING TOOL WITH RUBBER GRIP

CROSS-REFERENCE TO RELATED APPLICATION

This application claims the benefit of priority under 35 USC 119(e) of the filing date of U.S. Provisional Application Ser. No. 62/262,223, filed Dec. 2, 2015, which is hereby explicitly incorporated herein by this reference.

FIELD OF THE DISCLOSURE

The present disclosure relates to rotary torque applying tools, and more particularly to a torque applying tool having a torque limiting feature.

BACKGROUND

Some surgical procedures utilize small fasteners having limited torque applied thereto, such as those used to install pacemakers in patients. Torquing such small fasteners is problematic in that there are few if any tools that are adjustable to limit torques to very small values, in a tool which itself is quite small and delicate. Moreover, because of the surgical environment, a torque tool must be sterilized. Reuse of such tools is objectionable since a used torque tool must be carefully sterilized for a reuse, which requires valuable time of medical personnel. A sterilized tool must also be suitably repackaged, and tracked as part of inventory. These ancillary tasks make reuse of surgical torque tools unfeasible economically. There exists a need for a better way of providing small surgical torque tools.

SUMMARY

The disclosed concepts address the above stated situation by providing a torque tool which is utilized once and discarded. The possibility of transmitting infectious agents, sterilizing, repackaging, and tracking of a torque tool, with the attendant time demands on personnel, are all eliminated. Hence costs imposed on hospitals and other medical care facilities are minimized.

According to the present disclosure, there is described a torque applying tool suited for torquing small surgical fasteners. The tool includes a torque limiting clutch accessible when a housing of the tool is removed, so that torque limits can be sensed without subjecting the blade or working shaft to deforming forces. Torque can be adjusted by turning a nut threaded to the blade or working shaft. The torque limiting clutch is formed in interacting cam members bearing interacting ratchet surfaces, the cam members urged together by a spring located between the clutch and the housing, away from interference with torque sensing when first establishing a predetermined maximum torque of the tool. The tool is small and disposable, and includes a rubber grip coating.

It is an object to provide improved elements and arrangements thereof by apparatus for the purposes described which is inexpensive, dependable, and fully effective in accomplishing its intended purposes.

These and other objects will become readily apparent upon further review of the following specification and drawings.

BRIEF DESCRIPTION OF THE DRAWINGS

Various objects, features, and attendant advantages of the disclosed concepts will become more fully appreciated as the same becomes better understood when considered in conjunction with the accompanying drawings, in which like reference characters designate the same or similar parts throughout the several views, and wherein:

FIG. 1 is an exploded perspective view of a self-limiting torque applying tool, according to at least one aspect of the disclosure;

FIG. 2 is a cross sectional view of the self-limiting torque applying tool of FIG. 1, taken along a longitudinal plane;

FIG. 3 is a cross sectional view of the self-limiting torque applying tool, taken along a longitudinal plane perpendicular to that of the view of FIG. 2;

FIG. 4 is a cross sectional view of a self-limiting torque applying tool, taken along line C-C of FIG. 2; and FIG. 5 is a cross sectional view of a self-limiting torque applying tool, taken along line D-D of FIG. 2.

DETAILED DESCRIPTION

Referring initially to FIGS. 1-3, a self-limiting torque applying tool 100 comprises a hollow housing 7 including a grip surface 19 (FIG. 2), a longitudinal central axis (B-B, FIG. 2), a proximal end 23, a distal end 24, and a cap 10 rotatably engageable with the proximal end 23. A working shaft 9 is drivingly coupled to hollow housing 7 and is rotatable relative to hollow housing 7 about the longitudinal central axis B-B. A torque limiting clutch is operably between working shaft 9 and hollow housing 7. The torque limiting clutch is configured to enable transmission of torque from hollow housing 7 to working shaft 9, while limiting maximum transmitted torque to a predetermined value. Self-limiting torque applying tool 100 also comprises a torque adjuster operable to adjust the maximum transmitted torque to the predetermined value, and an adjusted torque sensing feature contained within hollow housing 7.

The torque limiting clutch may comprise an upper cam member 4 including a first ratchet surface 14 facing distal end 24 of hollow housing 7, and a lower cam member 2 including a second ratchet surface (e.g., a mirror image of first ratchet surface 14) facing proximal end 23 of hollow housing 7 and abutting first ratchet surface 14. The torque limiting clutch further comprises a spring 6 geometrically between lower cam member 2 and hollow housing 7. As employed herein, "geometrically between" refers to location of a component relative to other components. By contrast, "operably between" refers to a location along a path of torque as torque is transmitted from one component of the self-limiting torque applying tool 100 to other components. Spring 6 may be a metallic coil spring surrounding a portion of working shaft 9.

Unless otherwise indicated, the terms "first", "second", etc., are used herein merely as labels, and are not intended to impose ordinal, positional, or hierarchical requirements on the times to which these terms refer. Moreover, reference to, e.g., a "second" item does not either require or preclude the existence of, e.g., a "first" or lower-numbered item, and/or, e.g., a "third" or higher-numbered item.

Orientational terms such as upper and lower refer to the subject drawing as viewed by an observer, particularly, FIGS. 2 and 3. The drawing figures depict their subject matter in orientations of normal use, which could obviously change with changes in body posture and position. Therefore, orientational terms must be understood to provide semantic basis for purposes of description only, and do not imply that their subject matter can be used only in one position.

In the torque limiting clutch, working shaft 9 rotates in the clockwise direction when the preset torque value has been reached, causing spring loaded ratchet surfaces (e.g., ratchet surface 14) to disengage, thereby allowing rotation. The ratchet surfaces (e.g., 14) are an angled tooth design with abrupt or steep faces 20 (FIG. 1) at the rear of each tooth, which locks the rotation in the counter-clockwise direction of rotation. Lower cam member 2 traverses in an axial direction (relative to working shaft 9 and axis B-B) within hollow housing 7. Axial movement of lower cam member 2 allows disengagement of lower and upper cam members 2 and 4, thereby releasing working shaft 9 from torque inputs imposed on hollow housing 7 by hand.

As nut 5 is threaded onto working shaft 9 by engaging wrench surface 17 with a standard hex socket, and by rotation of nut 5, thus forcing upper cam member 4 to move axially against lower cam member 2, and causing compression of spring 6. Increasing or decreasing compression of spring 6 raises or lowers the force applied to lower and upper cam members 2 and 4. Cap 10 is applied to hollow housing 7 after completion of torque adjustment. Cap 10 is angularly positioned with an interfacing key 21 at proximal end 23 of hollow housing 7. Cap 10 is retained to hollow housing 7 by intermittent raised bumps which lock into an annular relief on the interior of hollow housing 7.

The adjusted torque sensing feature may comprise an outer surface comprising a wrench feature such as slot 11 in upper cam member 4. A wrench type torque sensing tool (not shown, but which may have for example inwardly projecting trunnions) can engage upper cam member 4 (e.g., by occupying slot 11) and sense torque applied thereto. It is contemplated that two slots 11 on opposed sides of upper cam member 4 will be provided for symmetrical loading and stability.

As working shaft 9 is intended for use with extremely small, high precision fasteners, it is of a small diameter, delicate, and thus vulnerable to damage. Hence, it is not recommended for connection to a torque measuring device during the initial torque setting adjustment. Slots 11 allow a tool to engage rotatable upper cam member 4 to rotate the assembly to set the required torque release value of self-limiting torque applying tool 100. Self-limiting torque applying tool 100 allows the user to check whether proper torque has been set by rotating upper rotating cam, rather than using the blade or working shaft 9. This is an important feature in light of the small size and delicate nature of working shaft 9. Working shaft 9 is not subjected to potentially distorting forces during setting of torque and testing.

It will be seen in FIGS. 2 and 3 that spring 6 is geometrically between lower cam member 2 and distal end 24 of hollow housing 7, thereby exposing the adjusted torque sensing feature for use in determining maximum transmitted torque applied to working shaft 9, in that slot 11 is not covered by spring 6.

In self-limiting torque applying tool 100, working shaft 9 may comprise a proximal end 25 including screw threads 12, and a distal end 26 including a working tip 27 configured to engage and drive a fastener (not shown), a nut 5 having screw threads 12 complementary to screw threads 3 of proximal end 25 of working shaft 9, and a wrench surface 17. Turning screw threads 12 of nut 5 selectively compresses and expands spring 6, thereby adjusting the maximum transmitted torque that will be transmitted by the torque limiting clutch. Turning screw threads 12 of nut 5 is of course performed by engaging wrench surface 17 with a suitable wrench and screwing nut 5 along working shaft 9. It should be appreciated that this is done with cap 10 removed, and with slot(s) 11 within easy reach, so that torque adjustments can be immediately checked. Working tip 29 may be of any drive configuration complementing the screws intended to be driven, such as Philips head, hexagonal, square, Torx®, etc.

Working shaft 9 extends through the torque limiting clutch and has a non-circular cross sectional configuration along a length of working shaft 9. Working shaft 9 is received in close cooperation with lower cam member 2 of the torque limiting clutch, such that rotation of the torque limiting clutch rotates working shaft 9. Flat surfaces 16 (FIG. 1) engage closely cooperating flat faceted hole 15 of upper cam member 4. Upper and lower cam members 4, 2 can therefore each translate along working shaft 9. However, only upper cam member 4 can also rotate about working shaft 9.

To this end, hollow housing 7 comprises at least one inwardly projecting rib 18 (FIG. 4). Lower cam member 2 comprises an equal number of grooves 13 (each) complementary in configuration to at least inwardly projecting rib 18. Hence lower cam member 2 is constrained to move only axially along the working shaft 9, and is constrained not to rotate relative to working shaft 9. Axial movement of lower cam member 2 accommodates compression and expansion of spring 6 when nut 5 is adjusted.

Working shaft 9 includes an enlargement presenting a thrust surface 8 (FIGS. 2 and 3) abutting hollow housing 7. Hollow housing 7 may be molded from a hard biocompatible plastic to receive the enlargement of working shaft 9 bearing thrust surface 8 in close cooperation.

Self-limiting torque applying tool 100 may further comprising a rubber covering 1 on an exterior surface of hollow housing 7. Rubber covering 1 may be ergonomically contoured, as seen in FIGS. 1-5. Rubber covering 1 allows for improved tactile manipulation during surgical procedures.

The torque adjuster may be configured to be adjustable as to maximum adjustable torque within a range of 0.5 to 4 inch pounds of torque. This value range is appropriate for the very small and delicate fasteners typically used in medical pacemakers (not shown).

To be appropriately sized for surgical duty, self-limiting torque applying tool 100 may have a length (i.e., along axis B-B, FIG. 2) of less than two inches and a maximum transverse dimension along the length of less than one inch.

To further assist in surgical procedures such as pacemaker implantation, cap 10 may comprise a shallow concave recess 28 facing away from tip 29 of working shaft 9. Shallow concave recess 28 is dimensioned and configured to receive an index finger (not shown) of a user, which is useful to steady and appropriately align self-limiting torque applying tool 100 by one finger. Self-limiting torque applying tool 100 is disposable, thereby achieving economies in the medical environment.

While the disclosed concepts have been described in connection with what is considered the most practical and preferred implementation, it is to be understood that the disclosed concepts are not to be limited to the disclosed arrangements, but are intended to cover various arrangements which are included within the spirit and scope of the broadest possible interpretation of the appended claims so as to encompass all modifications and equivalent arrangements which are possible.

I claim:
1. A self-limiting torque applying tool, comprising:
  a hollow housing including a grip surface, a longitudinal central axis, a proximal end, a distal end, and a cap rotatably engageable with the proximal end;

a working shaft drivingly coupled to the hollow housing and rotatable relative to the hollow housing about the longitudinal central axis;

a torque limiting clutch operably between the working shaft and the hollow housing, the torque limiting clutch configured to enable transmission of torque from the hollow housing to the working shaft while limiting maximum transmitted torque to a predetermined value;

a torque adjuster operable to adjust the maximum transmitted torque to the predetermined value; and an adjusted torque sensing feature contained within the hollow housing.

2. The self-limiting torque applying tool of claim 1, wherein the torque limiting clutch comprises:

an upper cam member including a first ratchet surface facing the distal end of the hollow housing; and a lower cam member including a second ratchet surface facing the proximal end of the hollow housing and abutting the first ratchet surface.

3. The self-limiting torque applying tool of claim 2, further comprising a spring geometrically between the lower cam member and the hollow housing.

4. The self-limiting torque applying tool of claim 3, wherein the spring is a metallic coil spring surrounding a portion of the working shaft.

5. The self-limiting torque applying tool of claim 4, wherein the adjusted torque sensing feature comprises an outer surface comprising a wrench feature in the upper cam member, whereby a wrench type torque sensing tool can engage the upper cam member and sense torque applied thereto.

6. The self-limiting torque applying tool of claim 5, the spring is geometrically between the lower cam member and the distal end of the hollow housing, thereby exposing the adjusted torque sensing feature for use in determining maximum transmitted torque applied to the working shaft.

7. The self-limiting torque applying tool of claim 3, wherein the working shaft comprises a proximal end including screw threads, and a distal end including a working tip configured to engage and drive a fastener, and a nut having screw threads complementary to the screw threads of the proximal end of the working shaft and a wrench surface, wherein turning the screw threads of the nut selectively compresses and expands the spring, thereby adjusting the maximum transmitted torque that will be transmitted by the torque limiting clutch.

8. The self-limiting torque applying tool of claim 7, wherein the working shaft extends through the torque limiting clutch and has a non-circular cross sectional configuration along a length of the working shaft, and is received in close cooperation with the lower cam member of the torque limiting clutch, whereby rotation of the torque limiting clutch rotates the working shaft.

9. The self-limiting torque applying tool of claim 3, wherein the hollow housing comprises at least one inwardly projecting rib, and the lower cam member comprises an equal number of grooves complementary in configuration to the at least inwardly projecting rib, whereby the lower cam member is constrained to move only axially along the working shaft and is constrained not to rotate relative to the working shaft.

10. The self-limiting torque applying tool of claim 3, wherein the working shaft includes an enlargement presenting a thrust surface abutting the hollow housing.

11. The self-limiting torque applying tool of claim 1, further comprising a rubber covering on an exterior surface of the hollow housing.

12. The self-limiting torque applying tool of claim 1, wherein the torque adjuster is configured to be adjustable as to maximum adjustable torque within a range of 0.5 to 4 inch pounds of torque.

13. The self-limiting torque applying tool of claim 1, wherein the self-limiting torque applying tool has a length of less than two inches and a maximum transverse dimension along the length of less than one inch.

14. The self-limiting torque applying tool of claim 1, wherein the cap comprises a shallow concave recess facing away from the tip of the working shaft, the shallow concave recess dimensioned and configured to receive one finger tip of a user.

15. The self-limiting torque applying tool of claim 1, wherein the self-limiting torque applying tool is disposable.

* * * * *